(12) United States Patent
Sawa

(10) Patent No.: US 9,341,613 B2
(45) Date of Patent: May 17, 2016

(54) DEVICE FOR SINGULATING AND DISPENSING RIGID AND SEMI-RIGID STRIPS

(76) Inventor: Kevin G. Sawa, Hanover Park, IL (US)

( * ) Notice: Subject to any disclaimer, the term of this patent is extended or adjusted under 35 U.S.C. 154(b) by 646 days.

(21) Appl. No.: 12/931,616

(22) Filed: Feb. 7, 2011

(65) Prior Publication Data

US 2012/0199601 A1  Aug. 9, 2012

(51) Int. Cl.
  *G07F 11/38* (2006.01)
  *A47F 1/12* (2006.01)
  *G01N 33/487* (2006.01)
  *B65D 83/08* (2006.01)

(52) U.S. Cl.
  CPC ...... *G01N 33/48757* (2013.01); *B65D 83/0811* (2013.01)

(58) Field of Classification Search
  USPC ............ 221/2, 4, 8, 154, 155, 208, 246, 252, 221/255, 256, 263, 268, 269, 277, 281, 288
  See application file for complete search history.

(56) References Cited

U.S. PATENT DOCUMENTS

| | | | |
|---|---|---|---|
| 3,874,564 A | 4/1975 | Huneke | |
| 4,197,965 A * | 4/1980 | Manz | 221/266 |
| 4,271,979 A | 6/1981 | Manz | |
| 5,489,414 A | 2/1996 | Schreiber et al. | |
| 5,510,266 A | 4/1996 | Bonner et al. | |
| 5,854,074 A | 12/1998 | Charlton et al. | |
| 5,989,917 A | 11/1999 | McAleer | |
| 6,872,358 B2 | 3/2005 | Hagen et al. | |
| 7,172,728 B2 | 2/2007 | Otake | |
| 7,337,918 B2 | 3/2008 | Fowler et al. | |
| 7,597,853 B2 | 10/2009 | West et al. | |
| 7,604,146 B2 | 10/2009 | Maissami | |
| 7,628,292 B2 | 12/2009 | Lancesseur | |
| 7,670,562 B2 * | 3/2010 | Sacherer | 422/562 |
| 2003/0186446 A1 | 10/2003 | Pugh | |
| 2007/0196240 A1 * | 8/2007 | Boozer et al. | 422/102 |
| 2010/0000905 A1 * | 1/2010 | Wang et al. | 206/569 |
| 2010/0140116 A1 * | 6/2010 | Stiene et al. | 206/204 |

* cited by examiner

*Primary Examiner* — Gene Crawford
*Assistant Examiner* — Kelvin L Randall, Jr.
(74) *Attorney, Agent, or Firm* — James P. Hanrath; George E. Bullwinkel

(57) ABSTRACT

A container device for storing, singulating and dispensing rigid and semi-rigid strips such as diagnostic test strips. A plurality of strips is contained and protected within a transparent container having an internal capture element for capturing and positioning a single strip adjacent a narrow normally-closed dispensing aperture. The aperture is exposed by rotating a spring-loaded container top cap to an open position. A detachable container base cap contains a desiccant and is replaceable. An optional stand stores the device in an upright position, and incorporates a tool to facilitate removal of the base cap for replenishing the container's contents or replacing the desiccant. A radio frequency identification (RFID) tag can be incorporated for electronic inventory control. The device can also be used as an integrated test strip container/single strip dispensing means for an automated analyte meter module.

21 Claims, 13 Drawing Sheets

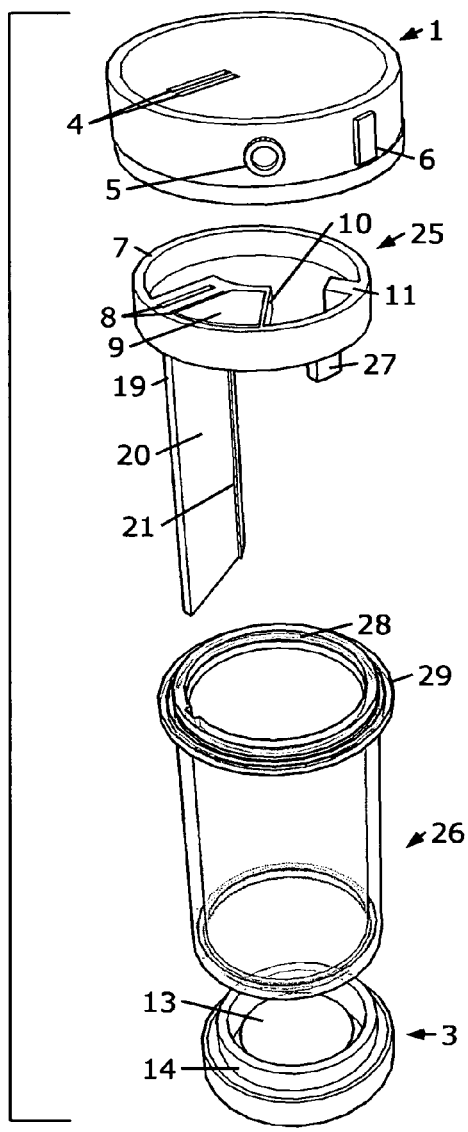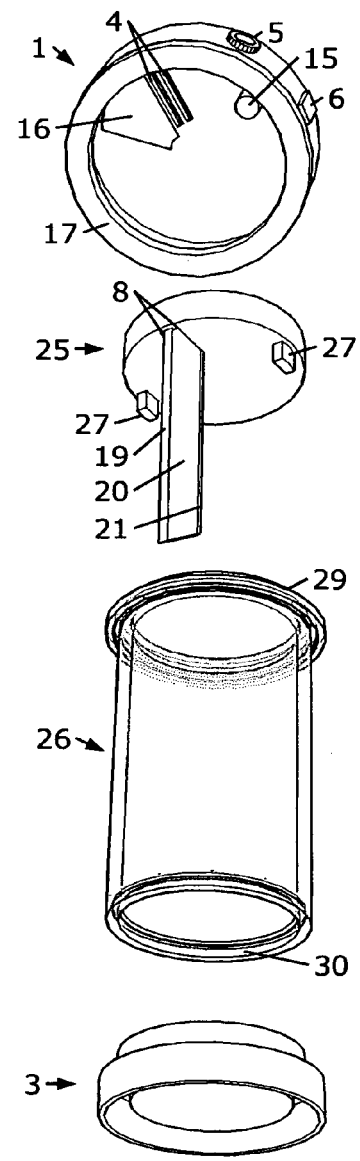
FIG.6
FIG. 6A

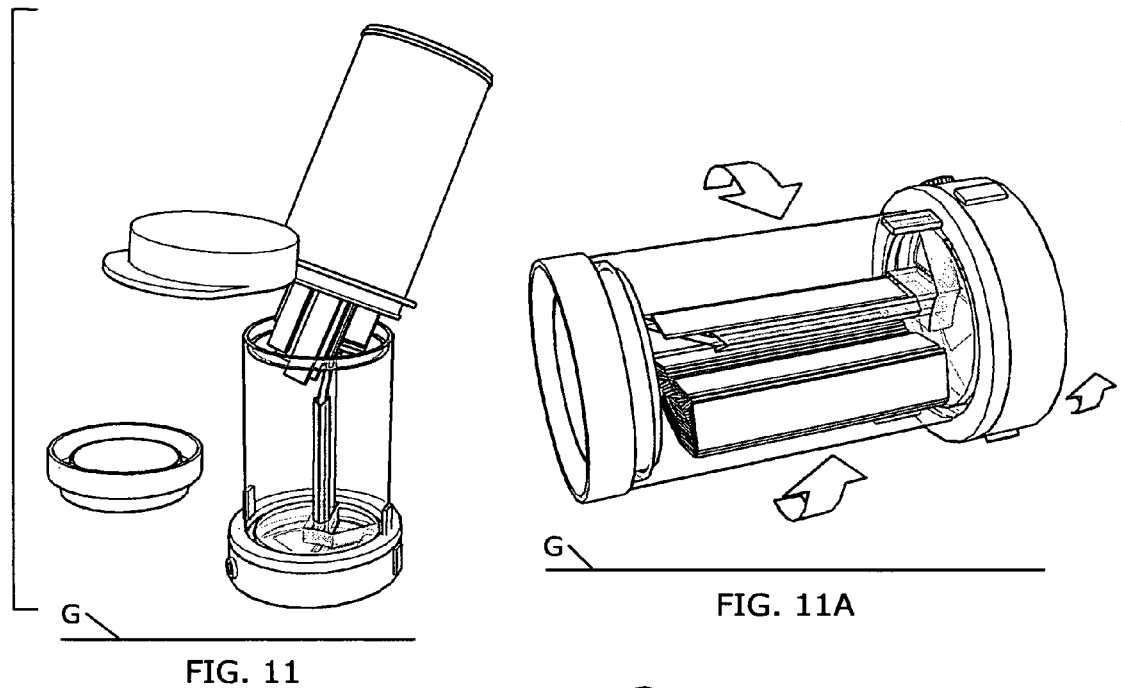
FIG. 11
FIG. 11A
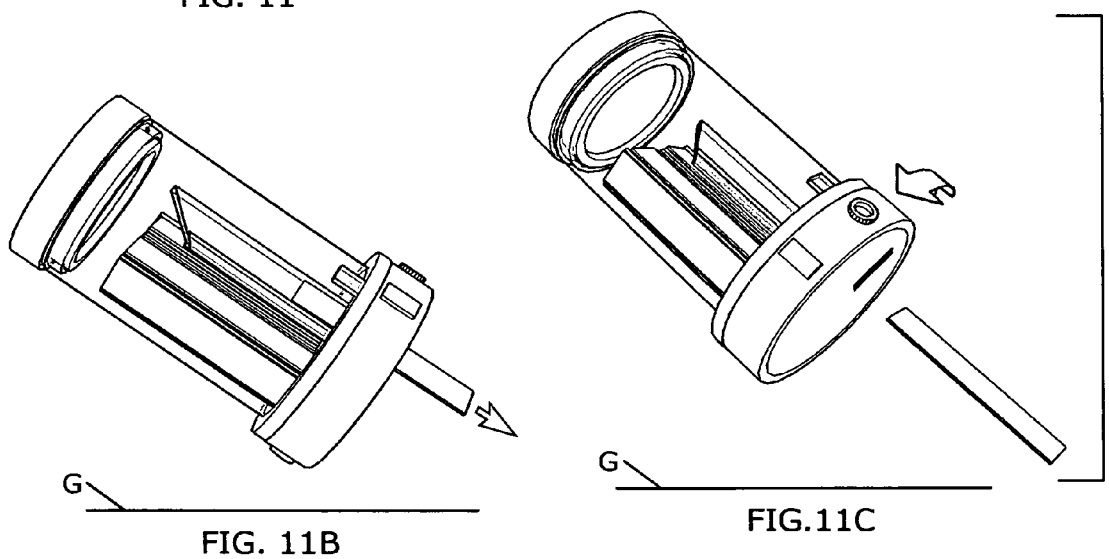
FIG. 11B
FIG. 11C

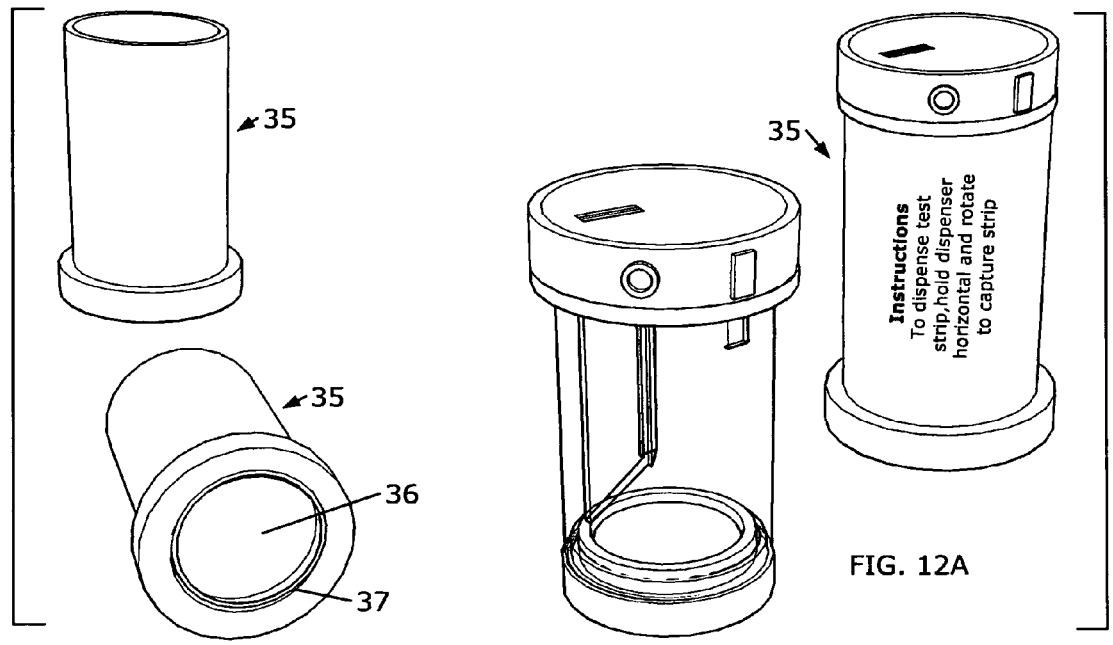
FIG. 12
FIG. 12A
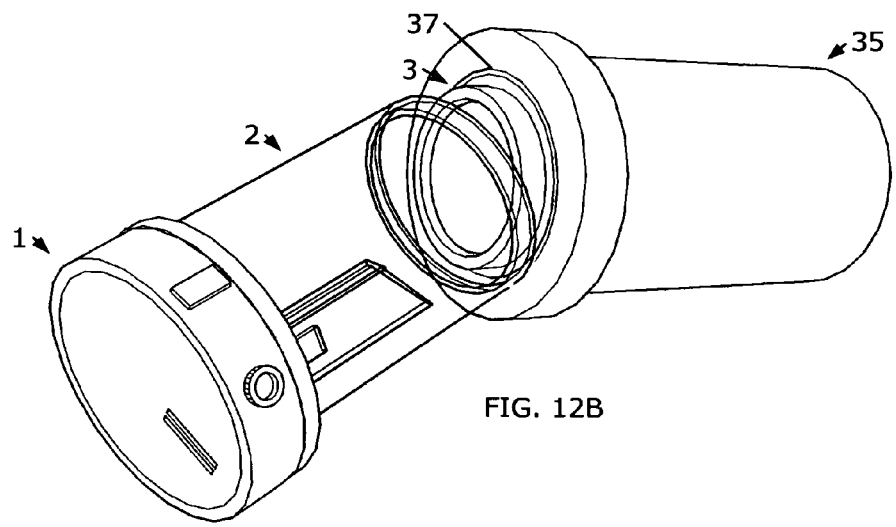
FIG. 12B

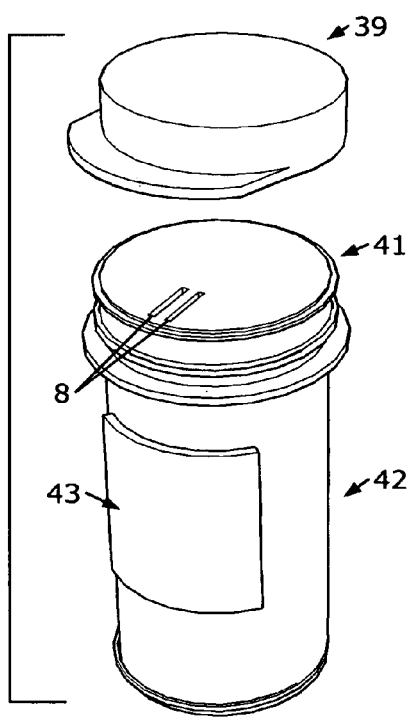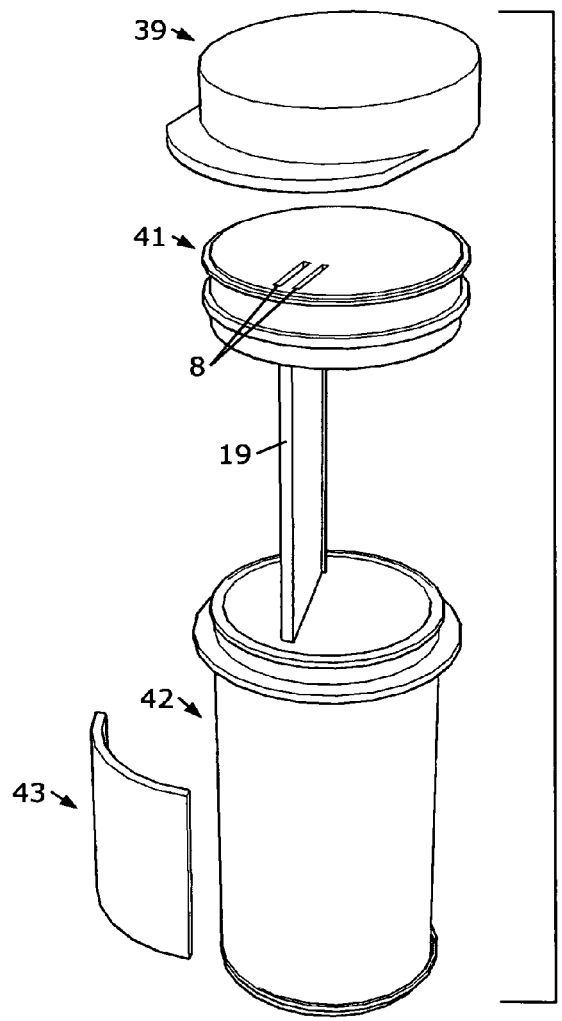
FIG. 14
FIG. 14A

DEVICE FOR SINGULATING AND DISPENSING RIGID AND SEMI-RIGID STRIPS

FIELD OF THE INVENTION

The invention relates to containers for protecting and dispensing one at a time, rigid and semi-rigid strips such as diagnostic test strips.

BACKGROUND OF THE INVENTION

Rigid and semi-rigid strips, such as test strips are used extensively in chemical analysis and medicine. For example, test strips are used to check for chemical concentrations or contaminants in water chemistry. In medicine, diagnostic test strips are used to measure analyte concentrations in biological fluids. Diagnostic test strips are commonly used by diabetics to monitor their blood glucose levels.

Such test strips are moisture sensitive and need to be protected from contaminants and maintained at appropriate humidity levels. They are usually stored in moisture resistant, polymer vials containing some sort of desiccant located in the cap or co-molded in the vial itself. Ideally, to avoid contamination, test strips should not be handled or touched before use.

Some diabetics have to check their blood glucose levels multiple times a day. The test strips are slippery and only a few millimeters in width and length. Due to the disease, diabetics may have diminished feel and eyesight. It is difficult for even those with good dexterity and eyesight to quickly extract a single test strip from a small vial that may contain up to 50 strips. The usual method requires inserting a finger into the vial to attempt sliding out a single strip, or tilting or shaking the vial to allow the test strips to slide half way out so a single test strip may be grasped and removed. These methods often lead to several test strips being touched and possibly contaminated by skin oils, etc. The test strips are also likely to fall out of the vial, damaging them or exposing them to dust and other contaminants. If returned to the vial, the contaminated strips could cross-contaminate the remaining strips. Also, the time required to manually grasp and remove a single test strip can allow the infiltration of airborne contaminants and moist ambient air into the open mouth of the usual vial container. This can degrade the reagent in the strips, compromising the quality of future tests. Such containers also commonly contain a desiccant, and the inadvertent intake of moisture can reduce its effective life.

Several complex test strip dispensers have been created to try to overcome some of the disadvantages associated with the simple test strip vials described above (see for example U.S. Pat. No. 5,489,414 to Schreiber et al; U.S. Pat. No. 5,510,266 to Bonner et al; U.S. Pat. No. 5,854,074 to Charlton et al and U.S. Pat. No. 5,989,917 to McAleer et al.) However, due to the complexity of these and other designs, the high cost of manufacture and assembly can put these devices out of the reach of the average user. Some more recent devices have been developed to try to reduce the number of required components, thereby lowering manufacturing costs (see for example U.S. Pat. No. 6,872,358 to Hagen et al; U.S. Pat. No. 7,172,728 to Otake; U.S. Pat. No. 7,597,853 to West et al; U.S. Pat. No 7,628,292 to Lancesseur et al; and U.S. Pat. No. 7,670,562 to Sacherer).

However, these devices suffer from certain disadvantages. Although the number of parts has been reduced, several are still mechanically complex and require considerable assembly of small parts. Most fail to maintain a constant moisture-free environment. Specifically, every time the caps and bases are separated to dispense a test strip, moisture and possible airborne contaminants are allowed, to some degree, to contact the test strips within. When the caps are replaced, the moisture inside the dispenser is sealed in and remains until the desiccant, if present, adsorbs it. These devices also fail to provide a means of monitoring the condition of the desiccant. If re-useable, most fail to describe the desiccant's eventual replacement. It is also difficult to determine the number of strips remaining inside the devices. And most provide no visual confirmation that a test strip has actually been selected until the cap is removed. Those that are reusable don't appear to be easily reloaded by the end user, or reloaded without touching and exposing the strips to outside contamination.

As a result, there continues to be a need for a simple, inexpensive device to singulate and dispense one at a time, rigid and semi-rigid strips such as test strips which are simple and inexpensive to manufacture, which maintain the integrity of their contents, are simple to reload, and have provision for an easily replaced desiccant.

SUMMARY OF THE INVENTION

A principal object of the present invention is to provide a simple, inexpensive, reusable container device to singulate and dispense one at a time, rigid and semi-rigid strips such as test strips. A further object is to provide such a device to store and protect the integrity of a plurality of strips from outside moisture and contaminants, and which is transparent, thereby allowing the user to easily view the position, orientation and number of the strips contained within, to confirm the capture of a single strip to be dispensed, and to view the condition of a replaceable desiccant. After the strips are loaded they are not touched or exposed to outside contaminants until they are actually dispensed for use, one at a time.

These and other objects of the invention are achieved by providing a device with a transparent container, an internal integrally molded planar capture element, and in the preferred embodiment, a partially rotatable spring-loaded cap having a narrow aperture through which the strips are conveniently dispensed one at a time. The container of the preferred embodiment has a removable base cap by which the container's contents may be replenished, and/or the desiccant can be replaced.

The device of the invention does not differ significantly in size from a conventional test strip storage vial, and therefore may be conveniently stored in a standard diabetes test kit.

The invention is described in several embodiments. In each embodiment the device singulates the test strips by singulating, through rotation along its longitudinal axis, at least one test strip on the planar surface of the capture element. When the dispenser is tilted top cap down, the singulated test strip is then guided along the planar surface by the capture ridge toward and then through the devices aligned apertures. The apertures are typically 97% smaller than the open mouth of the conventional test strip vial. This, plus short open times greatly reduce the potential for the infiltration of airborne contaminants and moist ambient air into the container. This maintains the relative humidity inside the container at a more constant state, better preserving the integrity of the contents.

In one embodiment, the device is comprised of three molded parts, is easily assembled and other than the partially rotating top cap, has no moving parts. The transparent storage container allows the user to hold the dispenser in a generally horizontal position and, with visual cues, manipulate the dispenser to capture and confirm that a single test strip is on the capture element. The top cap is then rotated to align the inner and outer apertures. In use, the dispenser is tilted, top cap down to dispense the test strip by gravity through the aligned apertures. The top cap is then rotated back to the closed, sealed position.

In another embodiment, the capture element and its proximal disk shaped top with its associated apertures is molded in one piece as an insert. This insert is contained within a transparent storage tube. The addition of the partially rotating top cap and the removable base cap forms the dispenser. In yet another embodiment, the partially rotatable top cap of the container incorporates a spring which, when the cap is opened to dispense a strip, biases the cap back to the closed, sealed position.

In still other embodiments, the capture element and its proximal disk shaped top with its associated apertures is molded in one piece as an insert for the conventional vial or a conventional vial molded in a transparent polymer. Various vial closures could be used.

In each of the disclosed embodiments, a desiccant may be provided within the container, preferably one which provides a visual indication to the user which can be observed through the transparent walls of the containers. Additionally, the addition of a radio frequency identification (RFID) tag or Bluetooth device allows electronic scanning and reading of information about the product, such as its manufacturer, date of manufacture and inventory information. The device can also be used as an integrated test strip container/single strip dispensing means for an automated analyte meter module.

In the described embodiments with a base cap, a stand is provided which is opaque and protects the contents of the transparent container from light, UV radiation and the like. A recess in the base of the stand is usable as a tool to assist in the removal of the dispenser's base cap.

BRIEF DESCRIPTION OF THE DRAWINGS

FIG. 6 shows details of the parts in FIG. 5 in an exploded perspective view.

FIG. 6A shows the underside of the top cap and an exploded distal perspective view of the parts in FIG. 5 with details of the capture element insert and storage tube.

FIG. 10B shows the same view as FIG. 10A with the container being rotated in the opposite direction to capture a single test strip 38a.

FIG. 11 shows the subject dispenser being loaded with test strips from a conventional test strip vial.

FIG. 11A shows the subject dispenser being rotated in a generally horizontal position relative to a horizontal plane G to singulate a single test strip on the capture element within. The top cap is then rotated to align the apertures.

FIG. 11B shows the subject dispenser being tilted top cap down, dispensing, by gravity, the captured test strip through the dispenser's apertures.

FIG. 11C shows the subject dispenser top cap down, test strip dispensed, with the top cap being rotated to offset the apertures, sealing the dispenser.

FIG. 12 shows a perspective and distal perspective view of the dispenser's opaque polymer stand.

FIG. 12A shows a subject dispenser and a subject dispenser in the optional stand.

FIG. 12B shows the stand's base cap removal recess being used as a tool to remove the dispenser's base cap.

FIG. 14 shows a perspective view of a fifth exemplary embodiment of the subject device as an insert for the conventional test strip vial. The vial's cap is shown removed to view the insert. An optional RFID tag 43 is shown attached to the outer surface of the dispenser.

FIG. 14A shows an exploded perspective view of the device in FIG. 14.

DETAILED DESCRIPTION OF THE INVENTION

As described below, each embodiment of the present invention describes devices which are reusable, have minimal components, contain, protect and maintain the integrity of a plurality of rigid and semi-rigid strips such as test strips, and dispenses the strips one at a time. The invention is suitable for dispensing all types of test strips, for example electrochemical, colorimetric and photometric type test strips.

The dimensions of the exemplary test strips referenced herein are provided with diabetes test kits, and are 6 mm wide by 32 mm long by 0.4 mm thick. They are described by way of example only, and the invention may be used with any rigid or semi-rigid strips of uniform shape without departing from the invention. In the present example, the dispenser in the form of a cylinder is 26 mm in diameter by 40 mm in height.

Conventional test strip vials are typically sized to hold up to 50 test strips. Thus the container of the present invention is similarly sized so that it may be conveniently stored in a standard kit with the accompanying glucose meter and lancet. The subject devices can also be sized to hold and dispense more test strips, but at the sacrifice of portability.

The device of the invention is easily reloaded by the user, as will be apparent from the descriptions below. It may also incorporate a removable base cap that may optionally contain a desiccant for maintaining the integrity of the container contents. The desiccant can be granular, polymer entrained or, preferably, a color-indicating polymer-entrained type. The desiccant might be co-molded or press fit into the base cap at time of manufacture. A color indicating polymer entrained desiccant is easily visible through the transparent storage container and its condition monitored by the user until replacement is indicated.

First Exemplary Embodiment (FIGS. 1, 2, 3 and 3A)

Figure 1:
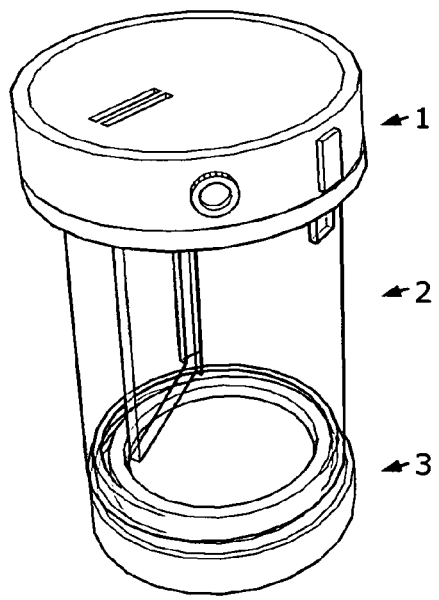
FIG. 1 shows a perspective view of a first exemplary embodiment of a dispenser according to the subject invention.

FIG. 1 shows an outside perspective view of the assembled first exemplary embodiment of the subject dispensers.

Figure 2:
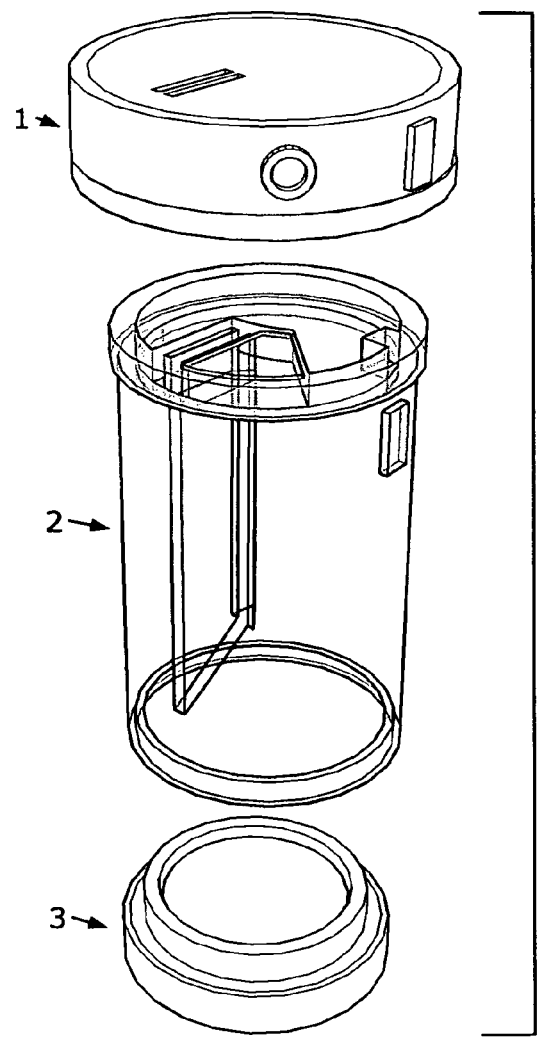
FIG. 2 shows an exploded perspective view of the subject dispenser in FIG. 1 with its constituent parts.

FIG. 2 shows an exploded perspective view of the dispenser in FIG. 1 with its constituent parts: a partially rotatable polymer top cap 1; a transparent polymer storage container 2; and a polymer base cap 3.

Figures 3, 3A:
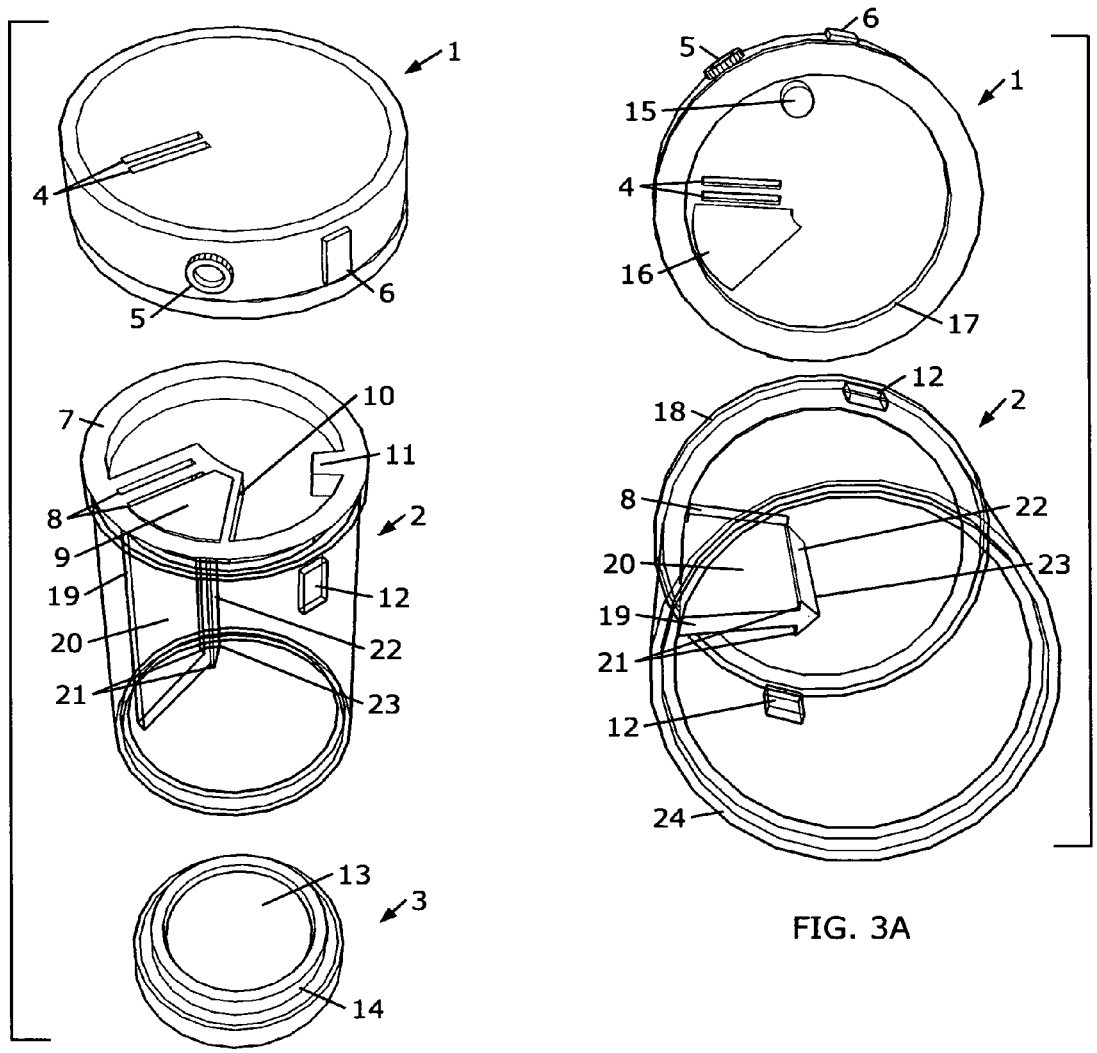
FIG. 3 shows details of the parts in FIG. 2 in an exploded perspective view with some surfaces rendered opaque for clarity.
FIG. 3A shows the underside of the top cap and a distal perspective view of the storage container in FIG. 2 with details of the associated capture element. Some surfaces are rendered opaque for clarity.

FIG. 3 shows details of the parts in FIG. 2 in an exploded, top perspective view. The top cap 1 is shown with its dual outer apertures (which can also be combined to form a single outer aperture) 4, and its closed 5 and open 6 status indicators. The outer apertures 4 may be sized slightly larger than the inner apertures 8 to insure unobstructed test strip dispensation.

The top of the storage container 2 is shown with the rotation bearing surface 7, dual inner apertures 8, the outer aperture sealing pad 9, the open rotation stop 10, and closed rotation stop lug 11. Also seen is one of the two top cap status indexes 12. The bottom cap 3 is shown with its optional desiccant 13, and the bottom cap convex sealing ridge 14.

FIG. 3A shows details of parts 1 and 2 from FIG. 2 in an exploded distal perspective view. The underside of the top cap 1 is shown with its rotation stop pin 15, inner aperture sealing pad 16 and internal locking rib 17. The distal view of the storage container 2 shows the containers external locking rib 18. Also shown is the capture element 19 with its associated details: planar surfaces 20, capture ridges 21, ramps 22 and leading edge 23. Also seen is the internal base cap retention groove 24.

The material of the top cap 1 is preferably selected from the following group of moldable polymeric materials consisting of polyethylenes (PE); polypropylenes (PP); polystyrenes (PS); acrylonitrile butadiene styrene copolymers (ABS) and styrene-acrylonitrile copolymers (SAN); polymethyl methacrylates (PMMA); polyvinyl chlorides (PVC); polycarbonates (PC); inherently conductive polymer (ICP) alloys and inherently dissipative polymer (IDP) alloys. The material of the container body 2 and bottom cap 3 are preferably selected from the same materials.

The top cap's internal locking rib 17 snaps over the transparent storage container's external locking rib 18. This forms an annular locking snap fit between the top cap 1 and the transparent storage container 2. Other than snapping on the base cap, this is the only assembly required on this first embodiment of the dispenser. The devices are cylindrical in shape to allow the use of the partially rotatable top cap. A snap-on top cap without apertures would allow the shape of the dispenser to take on various shapes, for example elliptical or oval, etc. The partially rotating cap is the preferred design because the top cap, with its small apertures, stays on the container reducing the chance of contaminants entering the dispenser, or the possible loss of the cap itself.

The top cap 1 seals the top of the transparent storage container 2 when the closed indicator 5 is aligned with its status index 12. This rotates the top cap 1 into the closed position. With this rotation, the device's outer and inner apertures 4, 8 are offset, the inner aperture seal pad 16 moves over the inner apertures 8 and, through tight frictional contact and elastic deformation, forms a substantially air-tight and moisture-tight seal. At the same time, the outer apertures 4 move over the outer aperture seal pad 9 and, through minimal contact and deformation, form an outer aperture dust seal. This keeps dust and other foreign particles out of the cavity formed between the top cap 1 and the top of the storage container 2. Because the quality of the seal between the inner apertures 8 and the inner aperture seal pad 16 takes priority over the seal between the outer apertures 4 and the outer aperture seal pad 9, the thickness of the inner aperture seal pad 16 is greater than the outer aperture seal pad 9. The leading edges of the sealing pads 9, 16 and the raised inner apertures are chamfered to facilitate the above movement. Since the contact area between the sealing pads and apertures is small, and because of the self lubricating properties of the materials, sufficient sealing pressure can be applied with relatively little torque. Positive aperture alignment and aperture offset are provided by the open rotation stop 10, the closed rotation stop lug 11 and the rotation stop pin 15 that moves between these two elements. Top cap position status is determined by viewing the position of the closed 5 and open 6 indicators relative to the top cap status index 12. The two indexes are molded on the outside of the storage container near the proximal end. This allows viewing the top cap status in the natural line of sight when a single test strip has been captured within. The user then rotates the dispenser through visual cues to capture a single test strip on the capture element as will be described in detail below.

Of the several moldable polymeric materials adapted for use with the storage container 2 of the present invention specified above, transparent acrylic is preferred for its combination of optical clarity, low UV transmission rate, low water absorption characteristics, strength and cost. It allows the user to view the number, placement and orientation of the test strips within.

Inside the container 2 is an integral capture element 19 internally disposed perpendicular to the inside wall of the container along its longitudinal axis. The capture element has two planar surfaces 20, two capture ridges 21, two ramps 22, and a leading edge 23. There are two associated apertures 8 at the proximal end of the capture element. The dimensions of the above mentioned capture element's features are dictated by the size of the test strips to be dispensed. As mentioned above, the dimensions of the test strips for the exemplary embodiment of the subject device are 6 mm wide×32 mm long×0.4 mm thick. This dictates a planar surface 20 width of 6.3 mm, a planar surface 20 length of 28 mm, a capture ridge 21 height of 0.3 mm, and an associated aperture 8 size of 0.5 mm high×6.4 mm wide. These dimensions allow only one test strip to be singulated and captured on the planar surface 20 of the capture element 19, and to be dispensed through the associated aperture 8. The dimensions stated above for the capture element details were selected to allow a single test strip to easily drop onto the planar surface 20 without a second strip becoming wedged perpendicular between the edge of the first strip and the container wall. These dimensions are the preferred dimensions for the above mentioned test strip size, and could be changed without departing from the scope and spirit of the invention.

The distal end of the capture element 19 is angled and beveled to reduce the chance of test strip hang up on its cross-section while the dispenser is being loaded. The primary purpose of the capture element 19 is to insure that only one test strip is oriented and then captured for dispensation. When more than one test strip rests on the planar surface 20, the weight and friction of the additional strips can prevent the first strip from sliding freely through the apertures.

Depending upon user manipulation, the capture element also divides, separates, guides, singulates, and reorients the test strips within. When engaged by the plurality of test strips 38 through rotation, the leading edge 23 divides and separates at least one test strip from the plurality of test strips. The surface of the ramp 22 then guides the test strip(s) up onto the planar surface 20 of the capture element. When the dispenser is rotated in the opposite direction, the capture ridge 21 allows all but one of the strips to slide off of the capture element 19. The top cap is rotated to the open position and tilted down. The captured and singulated test strip is then guided along the capture ridge 21 on the planar surface 20 and is dispensed, by gravity, through its associated aperture 8. The capture element 19 also reorients the plurality of test strips, if needed, when the dispenser is rotated at least 360°.

The capture element 19 is two-sided. That is, each side of the capture element is a mirror image of the other. This allows the dispenser to be used with the top cap, to the right or left based on user preference. Its preferred details and features give the capture element its distinctive arrow-shaped cross-section. The cross-section could be in the shape of half an arrow with one aperture, "L"-shaped with one aperture, "T"-shaped with dual apertures, and so forth without departing from the scope and spirit of the invention.

The distal end of the transparent storage container 2 has an internal groove 24 to receive the external convex rib 14 on the base cap 3. The groove 24 and rib 14 form intimate contact between the base cap 3 and the inside of the container 2 to form a substantially air- and water-tight seal. These types of seals are well known to those skilled in the art and, for conciseness, will not be detailed here. The base cap 3 material, like the top cap, is also selected from the group of moldable polymeric materials referred to above, and may also contain a desiccant, preferably a color-indicating polymer-entrained desiccant 13. The purpose of the desiccant is to maintain the humidity inside the dispenser at appropriate levels. The condition of the desiccant 13, if present, can be viewed and monitored through the transparent wall of the storage container 2. This base cap with desiccant could be easily replaced, only when needed, by the user. The base cap 3 needs only to be removed to allow the reloading of the dispenser, or to replace the desiccant. This ensures that the test strips are not touched or contaminated by airborne contaminants such as dust, oils from the skin, and the like, until they are actually dispensed for use, one at a time.

With reference to FIGS. 12, 12A and 12B, FIG. 12 shows a perspective view and a distal perspective view of the optional opaque stand 35. Also shown are the stand's base cap removal recess 36, and the base cap removal ridge 37.

FIG. 12A shows a perspective view of a subject dispenser, and a subject dispenser in the optional opaque stand 35. Instructions describing the use of the dispenser, the base cap removal recess and patent status could be screened, molded or applied as a label to the exterior of the stand.

FIG. 12B shows how the stand 35 could be used as a tool to assist in the removal of the dispenser's base cap 3. A user with limited hand or finger strength would place the dispenser with its attached base cap 3 in the recess 36 of the stand 35. With the removal ridge 37 in the gap between the storage container 2 and the base cap 3, the user would then use the stand to apply leverage to the base cap to easily release it from the dispenser.

The stand is described as optional as the dispenser is designed to be carried in the standard case with the meter and lancet in place of the original test strip storage vial. The case would protect the test strips contained in the dispenser from any possible UV radiation exposure. If the dispenser were not carried in the case, the dispenser could be placed in the stand 35 after use.

As a further feature of the invention, for the purpose of dissipating static electric charges which might otherwise cause the test strips 38 to cling to each other or to the inner elements of the container 2 and internal capture element 19, at least one of the body, top end, capture element and bottom end is made of a material selected from the group comprising inherently conductive polymer (ICP) alloys and inherently dissipative polymer (IDP) alloys. Also, the capture element 19 can be made of a conductive metal such as steel, magnesium, titanium, aluminum, brass and alloys thereof.

Second Exemplary Embodiment (FIGS. 4, 5, 6, 6A)

Figures 4, 5:
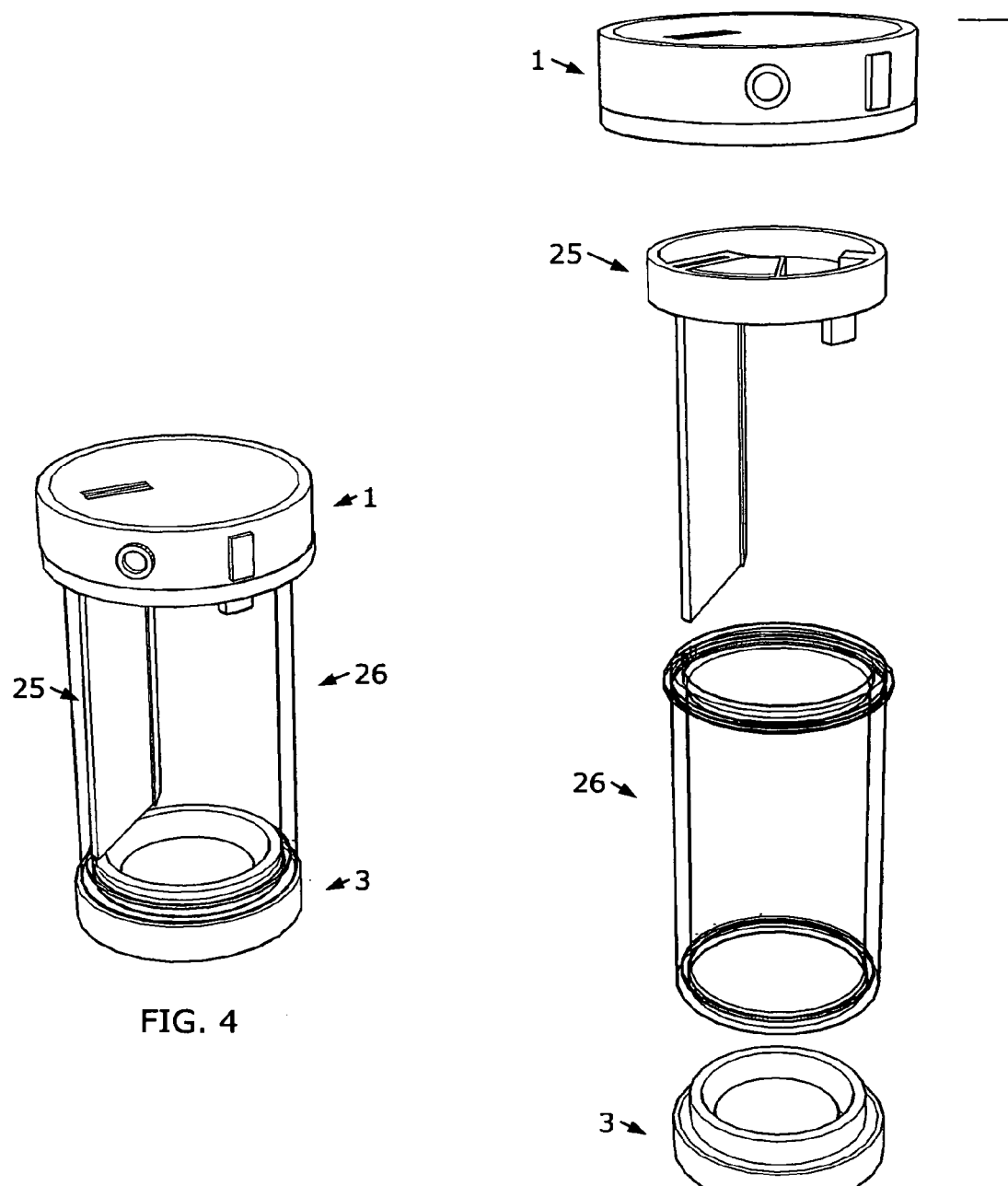
FIG. 4 shows a perspective view of a second exemplary embodiment of a dispenser according to the subject invention.
FIG. 5 shows an exploded perspective view of the subject dispenser in FIG. 4 with its constituent parts.

FIG. 4 shows an outside perspective view of the assembled second exemplary embodiment of the subject dispensers.

FIG. 5 shows an exploded perspective view of the dispenser in FIG. 4 with its constituent parts: a partially rotatable polymer top cap 1; an opaque polymer capture element insert 25; a transparent polymer storage tube 26; and a polymer base cap 3.

FIGS. 6 and 6A show details of the parts in FIG. 5. Only selected details of the insert 25 and the storage tube 26 will be described. Unless noted, all other components, features, details and methods are the same as described above in the first exemplary embodiment.

FIG. 6 shows the parts of FIG. 5 in an exploded perspective view. The top surface of the insert 25 is shown with the same details as the top surface of the storage container 2 described above in the first embodiment. The insert 25 has the capture element 19 from the first embodiment integrally molded with all of its associated details. It is distally disposed from between its associated inner apertures 8.

Unique to the insert 25 are two molded-in status indexes 27. These indexes 27 are located near the edge of the bottom surface of the insert 25. They are seen through the transparent wall of the storage tube 26 when the dispenser is assembled.

The insert 25 material is preferably selected from the group of moldable polymeric materials previously identified. It could also be molded in a preferred acrylic polymer of a dark color. This provides a contrasting background for the white test strips and makes it easier for a user with limited eyesight to confirm test strip capture on the capture element 19. As in the container of the first embodiment, the insert 25 may also be molded with different dimensions based on the size of the particular strip to be contained and dispensed.

The storage tube 26 is shown with its internal insert locking seat 28. The insert 25 can be installed in the locking seat 28 by means such as snap-fit, press-fit, ultrasonic weld, spin weld, bonding or screwing to create a storage container from the two parts with a mostly air- and moisture-proof seal. The storage tube also has an external locking rib 29. This rib interfaces with the top cap's internal locking rib 17 to form an annular locking snap fit between the top cap 1 and the storage tube 26.

The storage tube 26 material is also preferably selected from the group of moldable polymeric materials previously described. Preferably, it is molded in a transparent acrylic polymer. As in the first embodiment, this allows the user to visually manipulate the dispenser to singulate and capture a single test strip on the capture element, see the number of test strips remaining, and determine the condition of the desiccant, if provided, in the base cap.

FIG. 6A shows the parts in FIG. 5 in an exploded distal perspective view. The underside of the insert 25 shows both of the molded-in indexes 27. These indexes are molded-in to eliminate post mold painting or screening operations. The internal retention groove 30 is seen at the distal end of the tube 26. This groove 30 forms intimate contact with the base cap convex rib 14. This creates a substantially air- and moisture-proof seal. This type of seal is well known to those skilled in the art of the subject devices and, for conciseness, will not be detailed here.

Third Exemplary Embodiment (FIGS. 7, 8, 9, 9A)

Figure 7:
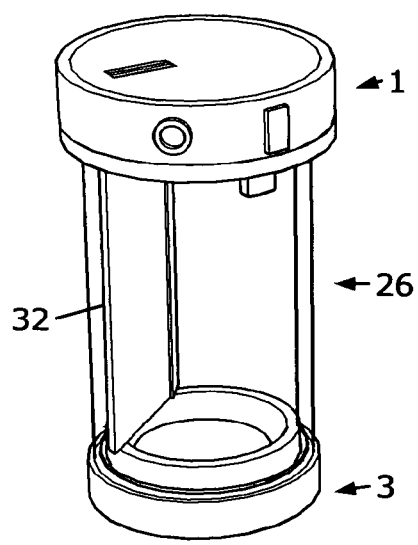
FIG. 7 shows a perspective view of a third exemplary embodiment of a dispenser according to the subject invention.

FIG. 7 shows an outside perspective view of the assembled third exemplary embodiment of the subject dispensers.

Figure 8:
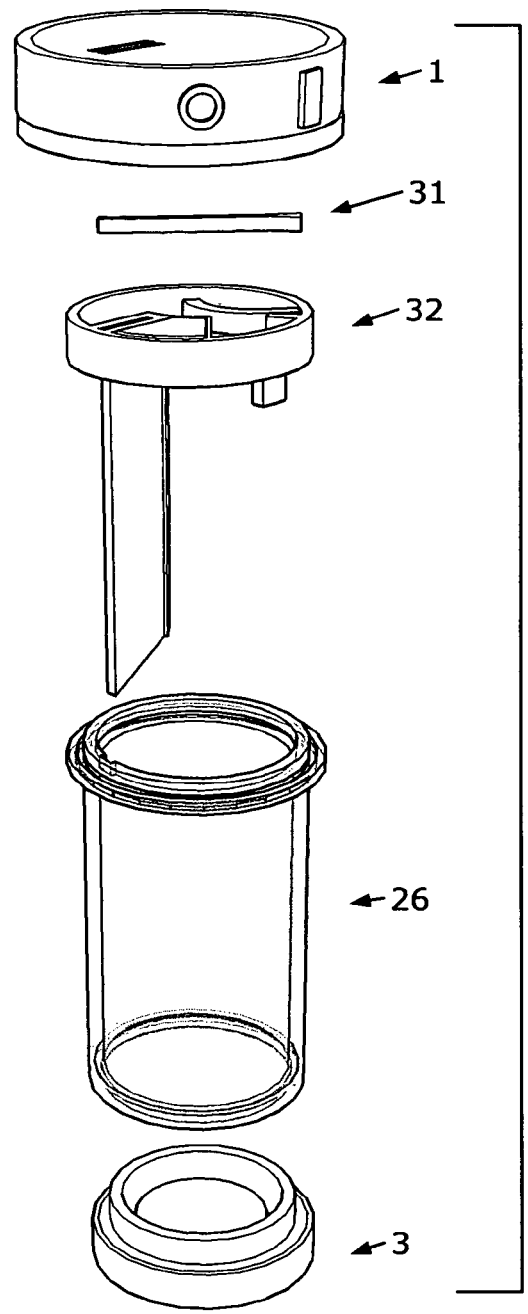
FIG. 8 shows an exploded perspective view of the subject dispenser in FIG. 7 with its constituent parts.

FIG. 8 shows an exploded perspective view of the dispenser in FIG. 7 with its constituent parts: a partially rotatable top cap 1; a spring 31; an opaque capture element insert 32; a transparent polymer storage tube 26; and a base cap with desiccant 3.

Figures 9, 9A:
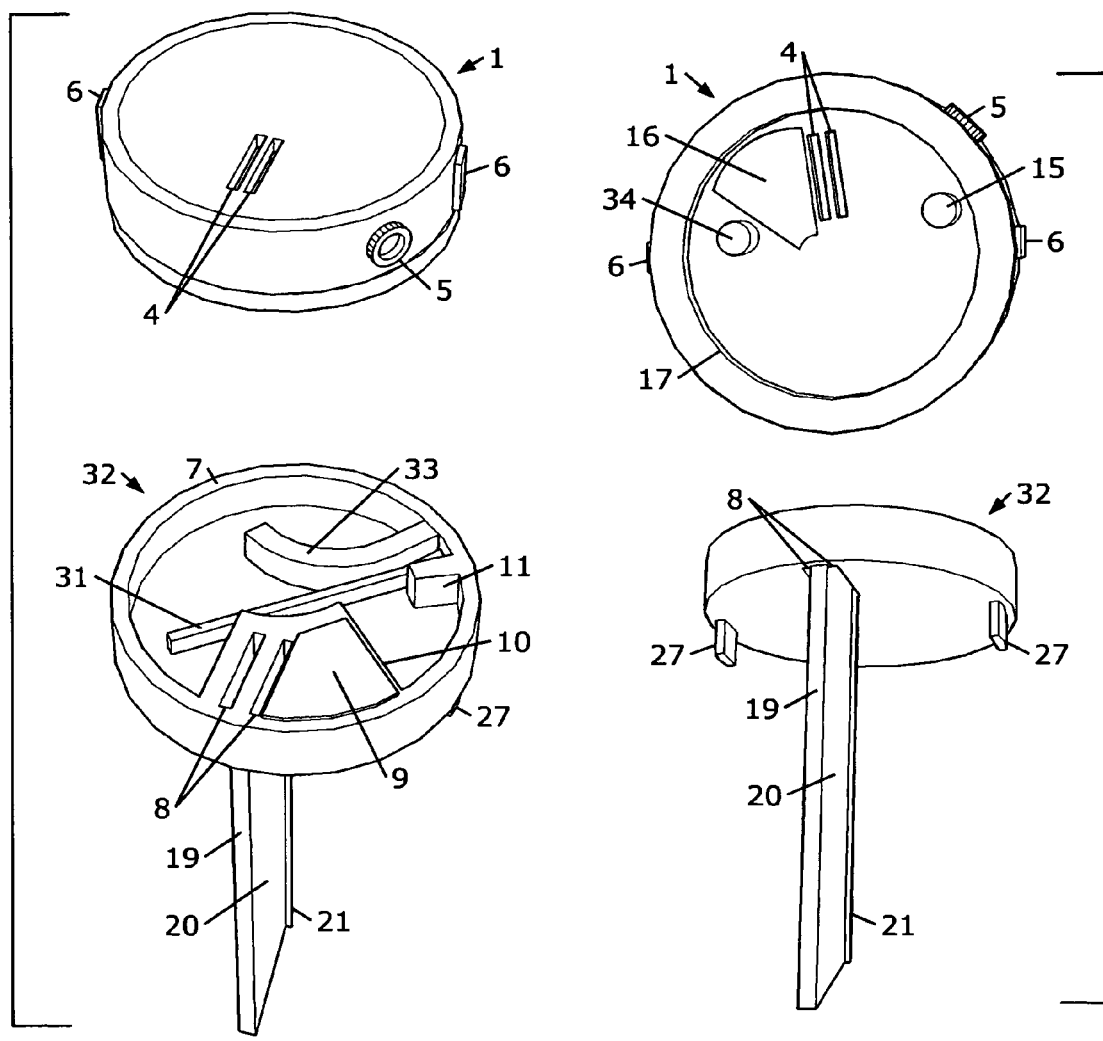
FIG. 9 shows a perspective view of the top cap and the top surface of the dispenser insert 32 in FIG. 8 with details of the polymer spring 31 and spring flex support 33.
FIG. 9A is a view of the underside of the top cap showing the addition of the spring engagement pin 34 and a distal perspective view of the insert 32 from the dispenser parts shown in FIG. 8.

Referring to FIGS. 9 and 9A. This third embodiment has all of the details and features of the second embodiment. Accordingly, only three new elements, the spring 31, the spring flex support 33, and the spring engagement pin 34 will be discussed in detail. The top surface of the insert 32 has the same details and features as the insert in the second embodiment described above. This insert, however, has the addition of a raised, molded spring flex support 33. The spring flex support 33 works in conjunction with the rotation stop lug 11 to contain the base of the cantilevered beam spring 31. The flex support 33 also removes stress from the base of the spring 31, and transfers it along the length of the spring.

The spring 31 in this example, is molded from the preferred polymer Delrin®, an acetal polymer. Its flexural strength, recovery from deformation, and resistance to fatigue would insure long service life. Its low coefficient of friction, combined with the small contact surface of the spring engagement pin 34, allows smooth operation with little felt resistance. When the assembled dispenser is in the closed position, the spring engagement pin 34 is in light contact with the spring 31. When a captured test strip is ready to be dispensed, the top cap is rotated to the open position, flexing and loading the spring 31. After the test strip is dispensed, the top cap is released, allowing the spring to return the top cap to the closed, sealed position.

The above details of this third embodiment could be applied to the top cap and top surface of the storage container of the first embodiment and the insert of the fourth embodiment as well.

Figure 13:
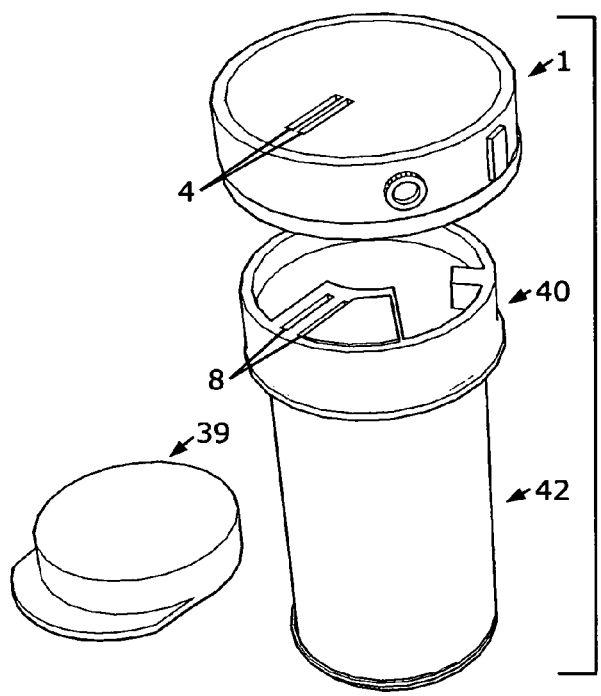
FIG. 13 shows a perspective view of a fourth exemplary embodiment of the subject device as an insert for the conventional test strip vial. It is shown with its partially rotating cap removed to view the insert.
Figure 13A:
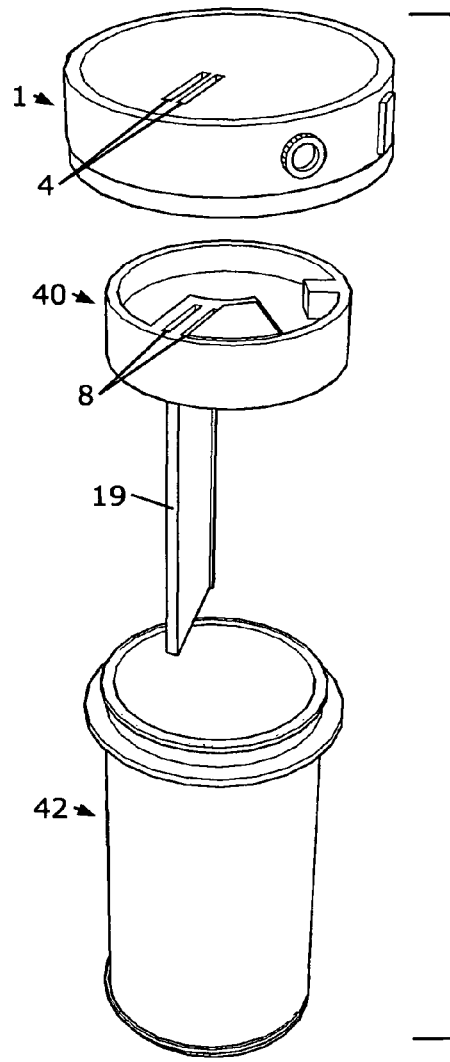
FIG. 13A shows an exploded perspective view of the device in FIG. 13

Fourth Exemplary Embodiment (FIGS. 13, 13A)

FIG. 13 shows a perspective view of a fourth embodiment of the device that is an insert for a conventional test strip vial.

The insert 40 is seen attached to the mouth of a conventional vial 42 to form a substantially air and moisture resistant seal. The vial's cap 39 is shown detached. The inserts cap 1 is removed to allow the insert to be seen. FIG. 13A shows an exploded perspective view of the device in FIG. 13. The insert 40 is shown with its capture element 19 with all of its details and proximal disk shaped top surface with associated apertures 8. It is molded with an annular interior groove (not shown) to snap onto the open mouth the vial 42. The top surface of the insert 40 has the same details as the top surface of the first embodiment's container and uses the same partially rotating top cap 1. To use this embodiment the user would rotate the top cap 1 to the open position. The vial would then be tilted top cap down to approximately a 45° angle and slowly rotated until a test strip, singulated by the capture element 19 is dispensed for use. The top cap 1 would then be rotated back to the closed, sealed position.

Fifth Exemplary Embodiment (FIGS. 14, 14A)

FIG. 14 shows a perspective view of a fifth embodiment that is also an insert. The insert 41 is seen attached to the mouth of a conventional test strip vial. The vial's cap 39 is removed to allow the insert to be seen. FIG. 14A shows an exploded perspective view of the device in FIG. 14. The insert 41 is shown with its capture element 19 with all of its details and proximal disk shaped top surface with associated apertures 8. The insert can be molded in a transparent polymer to allow the user to view the number of test strips remaining. The insert has a molded annular interior groove (not shown) to allow the insert to snap onto the mouth the vial 42 to form a substantially air and moisture resistant seal. The insert also has a molded annular exterior rib. This allows the vial's cap 39 to snap onto the top of the insert to seal the top of the assembly.

To use this embodiment the user would first snap off the top cap 39. The vial would then be tilted top cap down at approximately a 45° angle and slowly rotated until a test strip, singulated by the capture element 19 is dispensed for use. The top cap 39 is then snapped back onto the insert to re-seal the assembly. The cap 39 is shown as being detached from the vial 42. The cap of course could remain attached to the vial by a live polymer strap hinge or other attachment means. It is to be understood that the snap-on design of the fourth and fifth embodiments described above is for example only. The inserts could easily be adapted to any vial cap/closure shape or design such as oval, triangular, square, rectangular, screw on, etc.

If the above mentioned conventional opaque vials were molded in a transparent polymeric material, they would be used in the same manner as the first, second and third embodiments described above.

This embodiment includes an optional self-adhesive RFID (radio frequency identification) tag 43 attached to the outer surface of the vial 42 to enable electronic scanning and reading of information about the container and its product, such as the manufacturer and date of manufacture, for inventory control.

Figure 15:
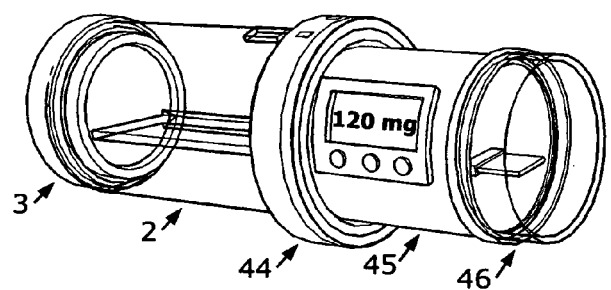
FIG. 15 shows the subject device coupled to an automated analyte meter module as an integrated test strip container and single strip dispensing means.
Figure 15A:
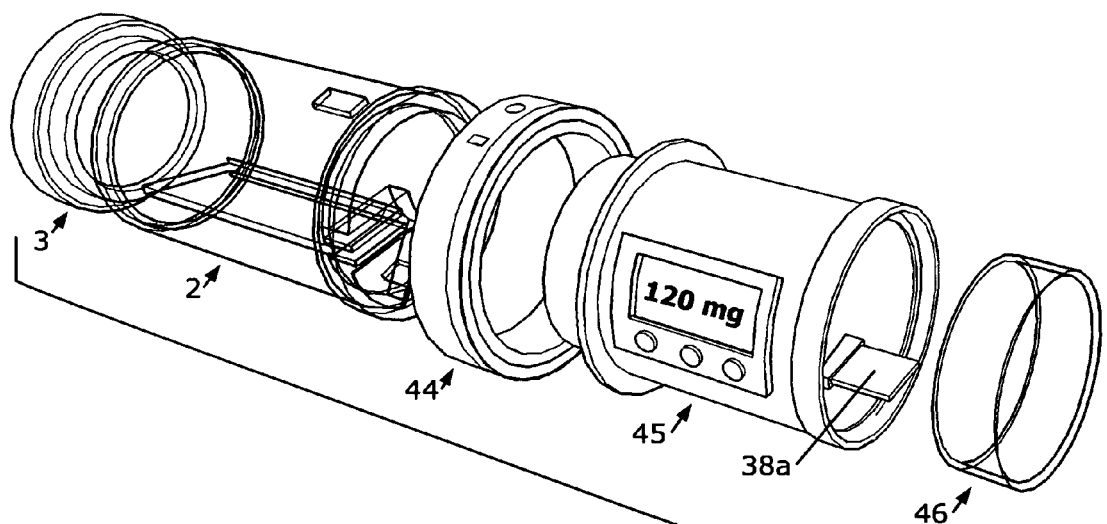
FIG. 15A shows an exploded perspective view of the device in FIG. 15.

Sixth Exemplary Embodiment (FIGS. 15, 15A)

FIG. 15 shows a perspective view of a sixth embodiment where the subject devices container 2 with its integral capture element 19 and base cap 3 are coupled to an automated analyte meter 45 as the meter's test strip container and single strip dispensing means. The container 2 is attached to the meter 45 with a coupling ring 44. Also seen is the test strip stop/end cap 46. FIG. 15A shows an exploded perspective view of the device in FIG. 15.

To use this embodiment the user would rotate the device as described below to capture a test strip on the capture element 19. The user would then rotate the meter 45 while holding the container 2 to align the containers aperture with the meter's aperture. The device would then be tilted meter end down to guide the test strip through the meter where it contacts the strip stop/end cap 46. This positions the test strip in the appropriate position in the meter for use. The meter is rotated back to offset the apertures, sealing the container. This action also moves the meter's internal contacts onto the test strip, gripping and holding the strip and activates the meter. The test strip stop/end cap is removed and the test is conducted as usual. After the test is completed, the test strip is simply grasped and removed, turning off the meter. The test strip stop/end cap is replaced and the device is ready for its next use.

Methods of Using the Dispenser

With reference to FIGS. 3, 3A, 10-10B, 11-11C, and 12. The method of use of the invention can be best understood. Before the dispenser can be used, it must be loaded with a supply of strips to be dispensed. One of the closed indicators 5 is rotated to align with its status index 12 on the storage container 2. This offsets the dispenser's apertures 4 and 8, sealing the top of the dispenser. The base cap 3 is then removed, and the dispenser is placed top cap down.

FIG. 11 shows a plurality of test strips (up to 50 in this example) being transferred into the dispenser. The base cap is replaced, sealing the bottom of the dispenser. It should noted that after the base cap is replaced, the contained test strips will not be touched or exposed to outside moisture or contaminants until they are actually dispensed for use, one at a time.

Figure 10:
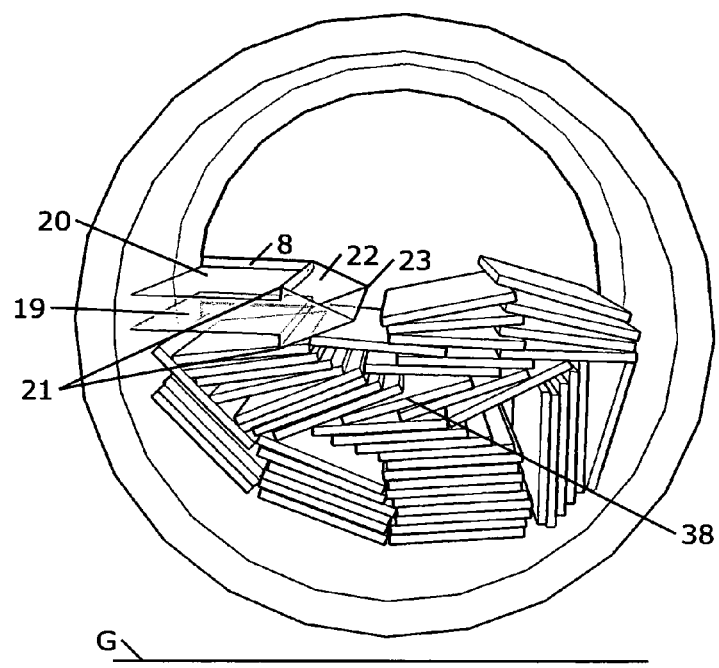
FIG. 10 is a distal view of the storage container in FIG. 2 in a horizontal position showing its capture element and the capture element's associated apertures 8. It also shows the plurality of test strips within.

FIG. 11A shows the dispenser in a generally horizontal position relative to a horizontal plane G. FIG. 10 shows a distal view of the transparent storage container 2 in a generally horizontal position relative to a horizontal plane G with its base cap removed for clarity. The internal capture element 19 is parallel to the ground on the side of the container away from the user. Its associated aperture 8 is seen at the proximal end of the capture element 19. The capture element's planar surfaces 20, two ridges 21, two ramps 22 and leading edge 23 are also seen, showing the capture element's arrow shaped cross-section. The plurality of test strips 38 are shown resting in the lower portion of the storage container.

Figure 10A:
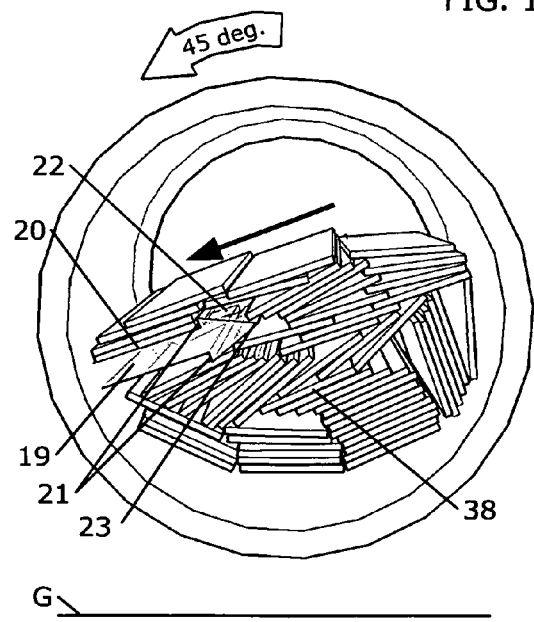
FIG. 10A shows the same view as FIG. 10 with the container being rotated to engage the plurality of test strips with the capture element 19.

FIG. 10A shows the upper surface of the horizontal storage container 2 being rotated away from the user 45° causing the plurality of test strips to slide, by gravity, to engage the leading edge 23 of the capture element 19. The leading edge 23 divides and separates at least one test strip from the plurality. The surface of the ramp 22, guides the strip(s) up on to the planar surface 20 of the capture element (black arrow). It should be noted that brisk rotation can increase test strip inertia to improve test strip capture. The additional inertia will help insure that the bottom-most strip will contact the container wall, allowing it to completely drop onto the planar surface of the capture element.

Figure 10B:
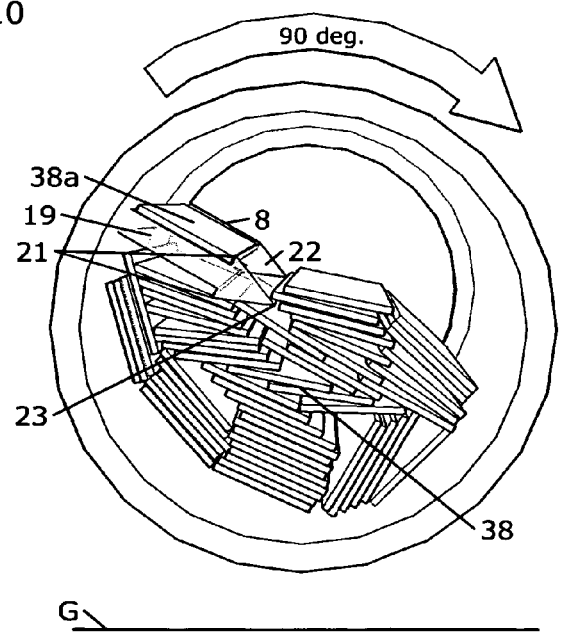

In FIG. 10B the user, seeing that at least one strip is on the planar surface of the capture element 19, reverses rotation 90° to allow all but one test strip 38a to slide off of the capture element. The user then has visual confirmation that only one test strip 38a is captured by the capture ridge 21. The single test strip 38a is now ready to be dispensed through the capture element's associated aperture 8. To reduce handling and possible contamination, the test strip could be dispensed into the clean, dry palm of the user's weak hand. That is, a right-handed person would dispense the test strip into the left palm where it is easily grasped by the right hand and inserted into the meter for testing.

As the number of test strips diminishes through use, the user, through visual cues, rotates the dispenser an increasing number of degrees in both directions to effect the test strip capture sequence described above. After the number of test strips in the dispenser drops to around 15, a second method of test strip capture can be used.

Referring to FIGS. 10C-10F, another method of manipulation is described.

Figure 10C:
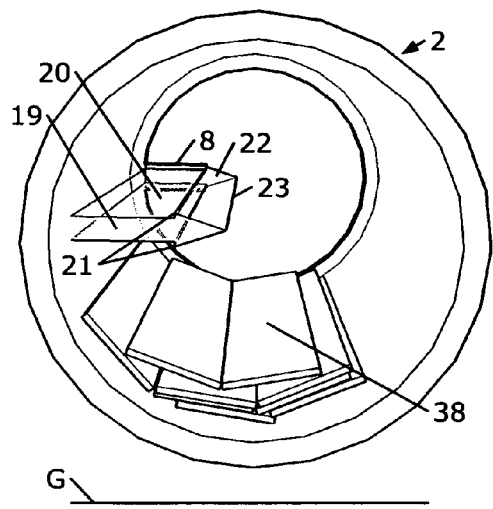
FIG. 10C shows a distal view of the storage container in FIG. 2 containing a limited number of test strips.

FIG. 10C shows a distal view of the storage container 2 being held in a generally horizontal position relative to a horizontal plane G. A limited number of test strips 38 are contained within. The base cap is removed for clarity. All elements and features of FIG. 10 are also seen in FIG. 10C.

Figure 10D:
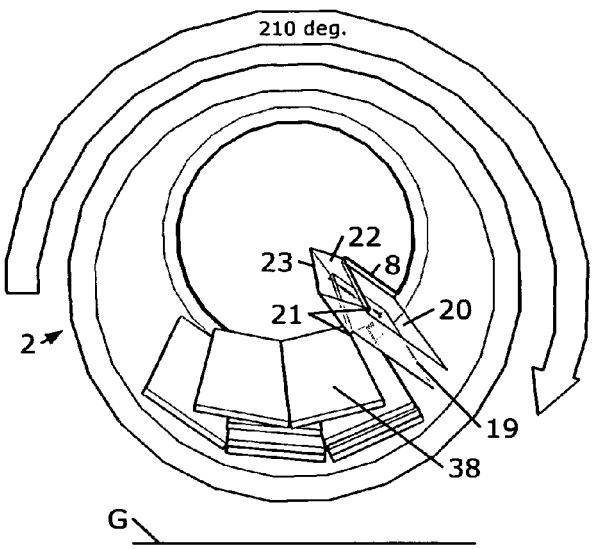
FIG. 10D shows the container in FIG. 10C being rotated to engage the capture element 19 with the test strips contained within.

FIG. 10D shows the top surface of the horizontal storage container being rotated toward the user 210° to engage the capture element 19 with the plurality of test strips 38 within.

Figure 10E:
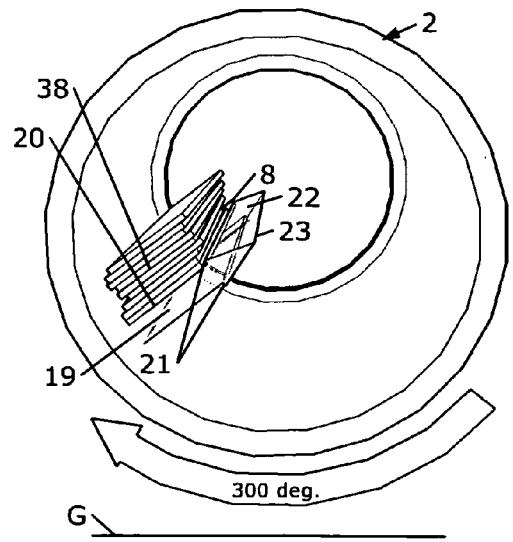
FIG. 10E shows the container in FIG. 10D being further rotated with the capture element 19 stacking the test strips contained within.

FIG. 10E shows continued rotation to 300° causing the capture element 19 to gather and stack the test strips 38 on the planar surface of the capture element 20.

Figure 10F:
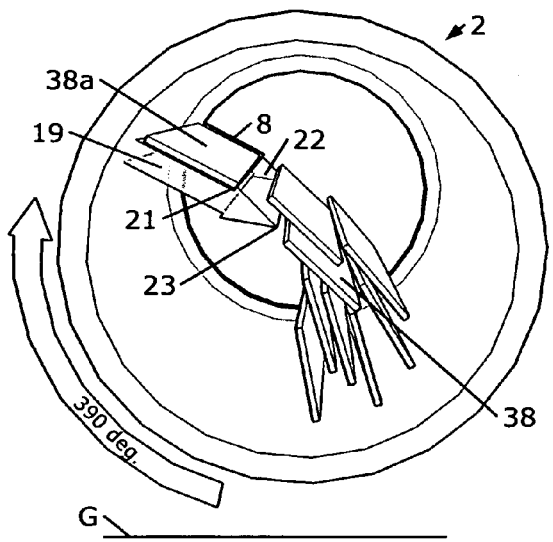
FIG. 10F shows the container in FIG. 10E being further rotated with all but one test strip 38a sliding off of the capture element.

FIG. 10F shows continued rotation to 390° where the capture ridge 21 allows all but one 38a of the gathered test strips 38 to slide, by gravity, off of the capture element 19. This single test strip is now ready to be dispensed through the capture elements associated aperture 8, as above, into the palm of the user's weak hand.

In FIG. 11A, after rotating the dispenser and capturing a single test strip, the user rotates the top cap to align the open indicator with its status index which aligns the dispenser's apertures.

In FIG. 11B, the dispenser is then tilted top cap down to allow the captured test strip to slide, by gravity, out through the aligned apertures in the dispenser's top.

In FIG. 11 C, the top cap is then rotated back to the closed, sealed position. The dispenser can then be placed in the standard kit case with the meter and lancet, or its optional opaque storage stand 35, as shown in FIG. 12A.

It should be noted that the number of degrees referenced above are for illustrative purposes only and are not meant to be limiting. The actual amount of rotation varies, and is determined by the user based on visually observing the number of test strips remaining, their current orientation, and their position relative to the capture element. It should also be noted that the above methods can be accomplished with the top cap to the user's right or left by utilizing either surface of the capture element.

As a commercial product, the dispenser of the present invention may be supplied with either a single supply of dispensable strips pre-loaded by a manufacturer for single use, or as a re-usable container in which the dispensable strips and desiccant may be replenished by the manufacturer or end user, allowing multiple uses.

It is evident from the above description that the above described invention provides a simple, reusable device that singulates and dispenses strips such as test strips one at a time. It has a number of advantages, including, but not limited to, improved contamination and moisture control, inexpensive manufacture through simple assembly with minimal parts, easy reloading and desiccant replacement, and simple, visually controlled use.

The invention claimed is:

1. A container for storing, singulating and dispensing to a user individual strips of rigid or semi-rigid material from a plurality of such strips comprising:
    (a) a container having a body with a vertical axis, top and bottom ends, and an outer wall forming said container, said container being operable to house a plurality of axially inserted strips of rigid or semi-rigid material in an aggregately loose and variable position or orientation therein, said top end having at least a first dispensing aperture sized to permit the passage of a single strip and said outer wall having an external container surface and an internal container surface,
    (b) closure means for selectively exposing said first dispensing aperture for the passage of a single strip, and
    (c) an internal capture element having a planar surface to engage a single strip thereon from said plurality of strips, said surface having a proximal portion adjacent said internal container surface and a radially inward extending portion distal said internal container surface, said capture element being aligned with said first dispensing aperture and having at least one capture ridge extending from said surface at said radially inward extending portion distal said internal container surface a height, said height of said capture ridge being approximately equal to or less than the thickness of a single strip when engaged on said surface,
    (d) wherein said internal capture element is operable to divide or separate, and reorient said aggregately loose plurality of strips in variable position or orientation within said container and is operable to capture and guide said single strip into said first dispensing aperture for grasping by a user.

2. The container of claim 1 in which said closure means comprises a cap having a second dispensing aperture, said cap being rotatable relative to said container body in a first direction for selectively bringing said first and second dispensing apertures into alignment for opening a passage for removal of a single strip, and rotatable in a second direction for closing said passage.

3. The container of claim 2 in which said cap includes biasing means urging rotation in said second direction for closing said passage upon release by a user.

4. The container of claims 1 or 2 in which said capture element is disposed perpendicular to said container inner wall.

5. The container of claim 1 or 2 in which said capture element has an arrow-shaped, a half arrow shaped, a "T"-shaped, or a "L" shaped cross-section.

6. The container of claim 1 or 2 in which said capture element has a distal end which is angled and beveled relative to the container vertical axis.

7. The container of claim 1 or 2 in which at least one of the body, top and bottom ends, inner wall and internal capture element is made of a static electricity-dissipating conductive polymer.

8. The container of claims 1 or 2 in which at least one of the body, top and bottom ends, inner wall and internal capture element is made of a moldable polymeric material.

9. The container of claim 1 or 2 in which at least one of the top end and internal capture element is made of a metal.

10. The container of claim 1 or 2 in which at least two of said body, top and bottom ends, and capture element are molded as an integral unit.

11. The container of claim 1 or 2 in which the contents are viewable by a user.

12. The container of claim 1 or 2 including a single supply of dispensable strips pre-loaded by a manufacturer for single use.

13. The container of claim 1 or 2 including a replenishable supply of dispensable strips which are loadable by a manufacturer for multiple uses.

14. The container of claim 1 or 2 including a replenishable supply of dispensable strips which are reloadable by an end user for multiple uses.

15. The container of claim 1 or 2 including an electronic tracking device for inventory control and usage monitoring.

16. The container of claim 1 in which said container includes an integral desiccant.

17. The container of claim 2 in which said bottom end comprises a removable base cap and further includes a stand for the container having a tool to assist in the removal of the base cap from the container.

18. The container of claim 17 in which a desiccant. is contained in said base cap.

19. The container of claim 17 in which said desiccant includes means for providing a visual indication of useful life.

20. The container of claim 1 or 2 in combination with an automated analyte meter means for dispensing a single said strip from the plurality of contained strips into the meter for use.

21. The method of singulating and dispensing individual strips of rigid or semi-rigid material, each strip having a thickness, comprising the steps of:
    (a) providing a container having a body with a vertical axis, top and bottom ends, and an outer wall forming said container, said outer wall having an external container surface and an internal container surface, said container being operable to house a plurality of axially inserted strips of rigid or semi-rigid material in an aggregately loose and variable position or orientation therein, said container having a strip dispensing aperture and including an internal capture element having a planar surface to engage a single strip thereon, said surface having a proximal portion adjacent said internal container surface and a radially inward extending portion distal said internal container surface, said capture element being aligned with said dispensing aperture and having at least one capture ridge extending from said surface at said radially inward extending portion distal said internal container surface a height, said height of said capture ridge being approximately equal to or less than the thickness of a single strip when engaged on said surface, wherein said internal capture element is operable to divide or separate, and reorient said aggregately loose plurality of strips in variable position or orientation within said container and is operable to capture and guide said single strip into said first dispensing aperture for grasping by a user;
    (b) inserting a plurality of said strips into said container;
    (c) manipulating said container to present a strip captured on said internal capture element to said strip dispensing aperture; and
    (d) dispensing said captured strip through said strip dispensing aperture.

* * * * *